US00PP14386P29

(12) United States Plant Patent
Anderson

(10) Patent No.: US PP14,386 P2
(45) Date of Patent: Dec. 16, 2003

(54) DAHLIA PLANT NAMED 'BALNOVRESE'

(50) Latin Name: *Dahlia pinnata*
Varietal Denomination: Balnovrese

(75) Inventor: Neil Anderson, St. Paul, MN (US)

(73) Assignee: Ball Floraplant, a division of Ball Horticultural Company, West Chicago, IL (US)

( * ) Notice: Subject to any disclaimer, the term of this patent is extended or adjusted under 35 U.S.C. 154(b) by 0 days.

(21) Appl. No.: 10/107,710

(22) Filed: Mar. 26, 2002

(51) Int. Cl.[7] ..... A01H 5/00
(52) U.S. Cl. ..... Plt./321
(58) Field of Search ..... Plt./321

*Primary Examiner*—Kent Bell
(74) *Attorney, Agent, or Firm*—Wood, Phillips, Katz, Clark & Mortimer

(57) ABSTRACT

A new and distinct Dahlia plant named 'Balnovrese', characterized by its yellow inflorescences with red accents and vigorous upright mounded growth habit is provided.

1 Drawing Sheet

Latin name of genus and species of plant claimed: *Dahlia pinnata.*
Variety denomination: 'Balnovrese'.

BACKGROUND OF THE INVENTION

The present invention comprises a new and distinct Dahlia plant, botanically known as *Dahlia pinnata* and hereinafter referred to by the cultivar name 'Balnovrese'.

The new cultivar originating as the product of the open pollination of plants from the seed variety *Dahlia pinnata* series 'Figaro Improved' (unpatented). The new Dahlia was discovered and selected as a single flowering plant from within the progeny of the above stated open pollination at Elburn, Ill. The new cultivar was initially designated PAS12202-8.

Asexual reproduction of the new cultivar by terminal or stem cuttings taken during 2001 at West Chicago, Ill., has demonstrated that the characteristics of the new cultivar as herein described are reproduced true to type through successive generations of such asexual propagation.

SUMMARY OF THE INVENTION

It was found that the cultivar of the present invention:

(a) forms double inflorescences with yellow ray florets with red accents;

(b) exhibits an upright mounded habit; and (c) exhibits a vigorous growth habit.

'Balnovrese' has not been observed under all possible environmental conditions to date. Accordingly, it is possible that the phenotype may vary somewhat with variations in the environment, such as temperature, light intensity, and day length without, however, any variance in genotype.

The new cultivar of the present invention can be compared to 'Margaret' (U.S. Plant Pat. No. 6,769). However, in side-by-side comparisons, 'Balnovrese' exhibits smaller inflorescences with fewer, smaller ray florets. The flowers of 'Balnovrese' are bicolor whereas those of 'Margaret' are solid.

BRIEF DESCRIPTION OF PHOTOGRAPH

The accompanying photograph shows as nearly true as it is reasonably possible to make the same in color illustrations of this type, typical inflorescence and foliage characteristics of the new cultivar. The plants were grown for nine weeks in a greenhouse at West Chicago, Ill.

DETAILED BOTANTICAL DESCRIPTION

The chart used in the identification of colors described herein is The R.H.S. Colour Chart of The Royal Horticultural Society, London, England. The color values were determined on Nov. 21, 2001 in West Chicago, Ill. The readings were taken between 10:00 and 11:45 p.m. under natural light conditions. The following observations and measurements describe plants grown in West Chicago, Ill., for nine (9) weeks after planting of rooted cuttings. The plants were produced from cuttings taken from stock plants and were grown in a double polycarbonate covered greenhouse under conditions comparable to those used in commercial practice. The plants were grown while utilizing a soilless growth medium and maintaining temperatures of approximately 65° to 70° F. (18° to 21° C.) during the day and approximately 60° to 65° F. (15° to 18° C.) during the night. Light levels of 4,000 to 6,000 footcandles were maintained. Plants were pinched at three weeks after planting.

Classification:
*Botanical.*—*Dahlia pinnata* cultivar 'Balnovrese'.
*Commercial.*—Dahlia.

Parentage: Open pollination within a selected population of plants from the series 'Figaro Improved'.

Propagation:
*Type cutting.*—Terminal tip.
*Time to initiate roots.*—Approximately 10 to 14 days.
*Time to develop roots.*—Approximately 21 to 28 days.
*Root description/habit.*—Fibrous and well branched.
*Tubers.*—Will form under short day conditions of at least 13 to 14 hours of darkness.

Plant description:
*General appearance and form.*—Upright mounded and vigorous.

*Height above pot.*—Foliage only: Approximately 12.7 cm. Whole plant: Approximately 22.3 cm.

*Width.*—Approximately 18.5 cm.

*Branching habit.*—Freely branching. Pinching 14 to 21 days after transplanting helps to improve basal branching.

*Branch description.*—Length: Approximately 10.1 cm. Diameter: Approximately 3 mm. Color: 144A with some anthocyanin coloration of RHS 183B. Texture: Smooth. Internode length: Approximately 1.5 cm.

Foliage description:

*Form.*—Mature foliage is simple.

*Shape.*—Ovate.

*Margin.*—Serrate.

*Apex.*—Acute.

*Base.*—Attenuate.

*Arrangement.*—Opposite.

*Venation pattern.*—Pinnate.

*Surface.*—Upper surface slightly rugose.

*Color of mature foliage.*—Upper surface: Darker than 137A with veins of 145A.

*Color of mature foliage.*—Lower surface: closest to 191A with veins of 145A.

*Size.*—Mature leaves are approximately 5.9 cm in length and approximately 3.7 cm in width.

*Petiole.*—Length is 9.6 mm. Diameter is 2.9 mm. Color is 145A.

Inflorescence description:

*Outdoor flowering habit.*—'Balnovrese' is freely flowering under outdoor growing conditions with substantially continuous blooming from spring through fall.

*Appearance.*—Fully double, arising from leaf axils on strong peduncles. Disc and ray florets arranged acropetally on a capitulum.

*Flower bud.*—Shape: Round. Length: Approximately 1.6 cm. Diameter: Approximately 1.6 cm. Color: 151B.

*Number per plant.*—Approximately four (4).

*Diameter.*—Approximately 6.8 cm. Depth: Approximately 2.3 cm. Disc diameter: Approximately 1.9 cm. Receptacle diameter: Approximately 2.6 cm. Receptacle height: Approximately 4 mm. Response time: Approximately six (6) weeks. Lastingness of Bloom: Approximately ten (10) days. Fragrance: None.

*Ray florets.*—Quantity: Approximately 24.2 per inflorescence. Shape: Elongated, cupped. Length: Approximately 2.7 cm. Width: Approximately 1.9 cm. Apex: Pointed to slightly rounded. Base: Attenuate. Margin: Entire. Texture: Smooth. Color: Fully opened, upper surface: 1A with 34C and venation of 34A at apex. Fully opened, lower surface 1B.

*Disc florets.*—Number per Inflorescence: Approximately 43. Shape: Elongated, cylindrical. Length: Approximately 1.1 cm. Diameter: Approximately 4 mm. Color: 3A at apex, 150D at base.

*Peduncle.*—Strong, erect. Length: Approximately 10 cm. Diameter: Approximately 2.2 mm. Texture: Smooth. Color: 144A.

*Involucral bracts.*—Quantity: 5. Shape: Diamond-shaped. Length: Approximately 1 cm. Width at Widest point: Approximately 6 mm. Base: Flat. Tip: Broadly acute. Margin: Entire. Texture: Smooth. Color of both upper and lower surfaces: 139A.

*Reproductive organs.*—Androecium — On disc florets. Stamen number: 4. Anthers approximately 2 mm in length, 168B. Pollen: Amount: Moderate. Color: 21B. Gynoecium — On disc and ray florets, Pistil number: One (1) per flower. Pistil length: Approximately 1.3 cm. Stigma length is 3 mm and color is 13A. Style length is 8 mm and color is 154C. Ovary length is 2 mm and color is 145B.

*Seed production.*—Seed production has not been observed.

*Disease resistance.*—Disease resistance has not been observed.

*Weather tolerance.*—The weather tolerance of the new Dahlia has been shown to be typical for Dahlias.

*Hardiness zone.*—'Balnovrese' is hardy in zones nine (9) and above.

In the claim:

1. A new and distinct cultivar of Dahlia plant named 'Balnovrese' substantially as herein shown and described, which:

(a) forms double inflorescences with yellow ray florets with red accents;

(b) exhibits an upright mounded habit; and (c) exhibits a vigorous upright mounded growth habit.

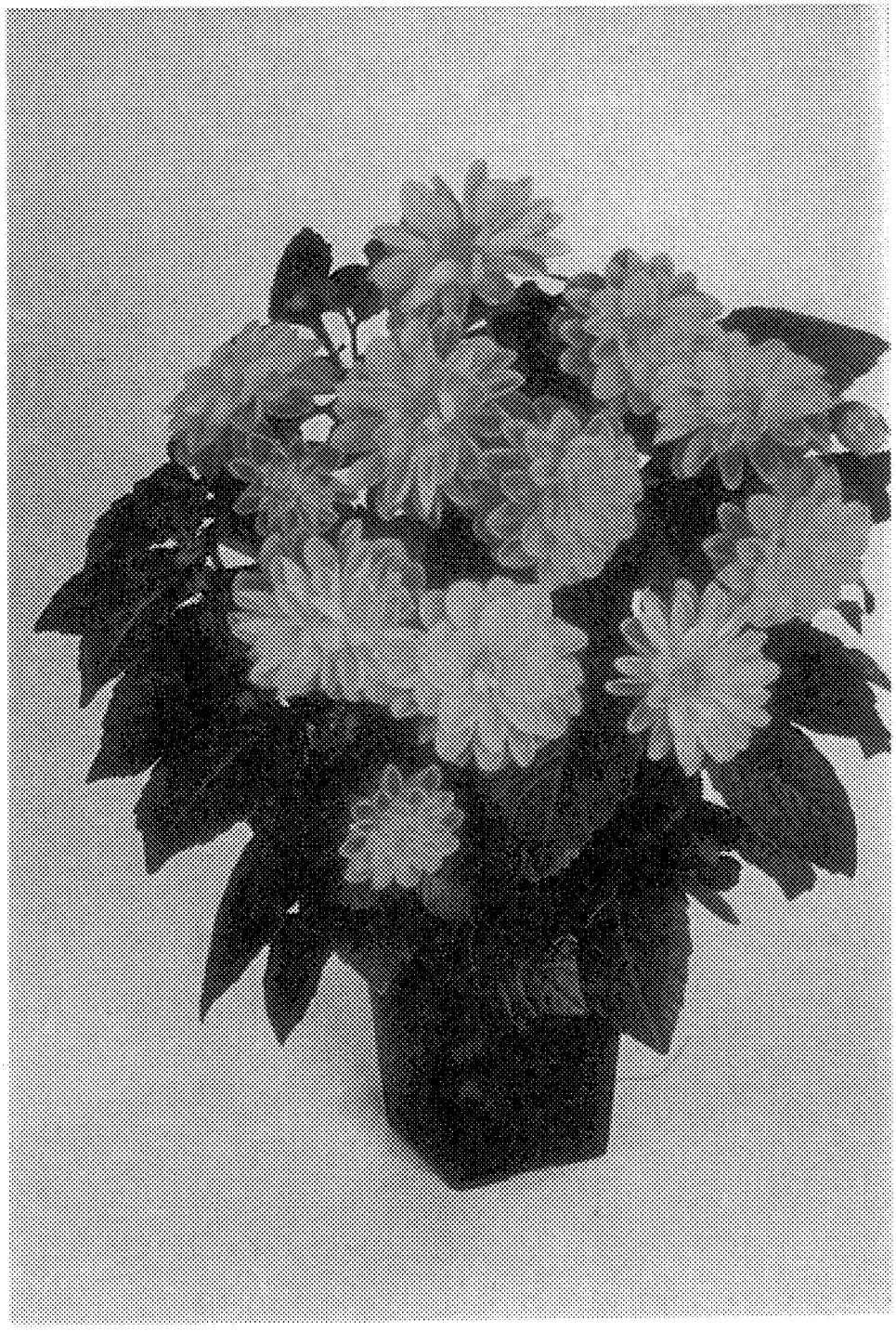

* * * * *